United States Patent [19]
Jao et al.

[11] Patent Number: 5,876,750
[45] Date of Patent: Mar. 2, 1999

[54] EFFECTIVE THERAPY FOR EPILEPSIES

[75] Inventors: Frank Jao, San Jose; Patrick S.-L. Wong, Palo Alto; Evangeline Cruz, Hayward; Eduardo C. Sy, Union City; Anthony L. Kuczynski, Mountain View, all of Calif.

[73] Assignee: ALZA Corporation, Palo Alto, Calif.

[21] Appl. No.: 871,075

[22] Filed: Jun. 9, 1997

Related U.S. Application Data

[62] Division of Ser. No. 439,915, May 12, 1995, abandoned, which is a continuation of Ser. No. 234,092, Apr. 28, 1994.

[51] Int. Cl.$^6$ .............................. A61K 9/52; A61K 9/20; A61K 9/24; A61K 31/415
[52] U.S. Cl. ........................ 424/457; 424/465; 424/473; 514/389; 514/964
[58] Field of Search .................... 424/457, 473, 424/465; 514/389, 964

[56] References Cited

U.S. PATENT DOCUMENTS

| | | | |
|---|---|---|---|
| 2,799,241 | 7/1957 | Wurster .................................. 118/24 |
| 3,845,770 | 11/1974 | Theeuwes et al. ...................... 128/260 |
| 3,916,899 | 11/1975 | Theeuwes et al. ...................... 128/260 |
| 4,063,064 | 12/1977 | Sanders et al. ..................... 219/121 L |
| 4,088,864 | 5/1978 | Theeuwes et al. ............... 219/121 LM |
| 4,160,020 | 7/1979 | Ayer et al. ............................... 424/15 |
| 4,200,098 | 4/1980 | Ayer et al. ............................. 128/260 |
| 4,285,987 | 8/1981 | Ayer et al. ................................. 427/3 |
| 4,327,725 | 5/1982 | Cortese et al. ......................... 128/260 |
| 4,485,087 | 11/1984 | Otsuko et al. ............................ 424/28 |
| 4,612,008 | 9/1986 | Wong et al. ............................ 604/892 |
| 4,765,989 | 8/1988 | Wong et al. ............................ 424/473 |
| 4,783,337 | 11/1988 | Wong ...................................... 424/468 |
| 4,857,336 | 8/1989 | Khanna et al. ......................... 424/473 |
| 5,091,190 | 2/1992 | Kuczynski .............................. 424/473 |
| 5,160,744 | 11/1992 | Jao et al. ................................ 424/473 |
| 5,190,763 | 3/1993 | Edgren et al. .......................... 424/473 |
| 5,190,765 | 3/1993 | Jao et al. ................................ 424/473 |
| 5,192,550 | 3/1993 | Edgren et al. .......................... 424/473 |
| 5,252,338 | 10/1993 | Jao et al. ................................ 424/473 |
| 5,284,662 | 2/1994 | Koparkar et al. ...................... 424/473 |
| 5,348,746 | 9/1994 | Dong et al. ............................ 424/473 |
| 5,660,861 | 8/1997 | Jao et al. ................................ 424/465 |

FOREIGN PATENT DOCUMENTS

| | | | |
|---|---|---|---|
| 0277092 | 8/1988 | European Pat. Off. ......... A61K 9/22 |
| 2148712 | 6/1985 | United Kingdom ............. A61K 9/00 |
| 2155889 | 10/1985 | United Kingdom ............. A61K 9/48 |
| 2182559 | 5/1987 | United Kingdom ............. A61K 9/22 |
| 2193632 | 2/1988 | United Kingdom ............. A61K 9/52 |
| WO92/18102 | 10/1992 | WIPO .............................. A61K 9/00 |
| WO94/27587 | 12/1994 | WIPO ............................ A61K 31/13 |
| WO95/06460 | 3/1995 | WIPO .............................. A61K 9/00 |

OTHER PUBLICATIONS

Guinchedi, P., et al., "Linear Extended Release of a Water--insoluble Drug, Carbamazepine, from Erodible Matrices," Intl. J. Pharm., vol. 94, pp. 15–22, 1993.

Windholz, M., Editor, The Merck Index, 10th Ed., pp. 1054–1055, abstract No. 7204, 1983.

Wurster, Dale E., "Air–suspension Technique of Coating Drug Particles," J. Amer. Phar. Assoc. Sci. ED., vol. 48, 1959.

Wurster, Dale E., "Preparation of Compressed Tablet Granulations by the Air–suspension Technique II," J. Amer. Pharm. Assoc., vol. 29, No. 2, 1960.

Remingtons Pharmaceutical Sciences, 14th Ed., pp. 1626–1680.

*Primary Examiner*—Kevin E. Weddington
*Attorney, Agent, or Firm*—Paul L. Sabatine; Michael J. Rafa; Pauline Ann Clarke

[57] ABSTRACT

A dosage form is disclosed for delivering an antiepileptic drug, which dosage form comprises a laminated wall for maintaining the integrity of the dosage form and of the antiepileptic drug.

2 Claims, 5 Drawing Sheets

FIG. 1
FIG. 2
FIG. 3
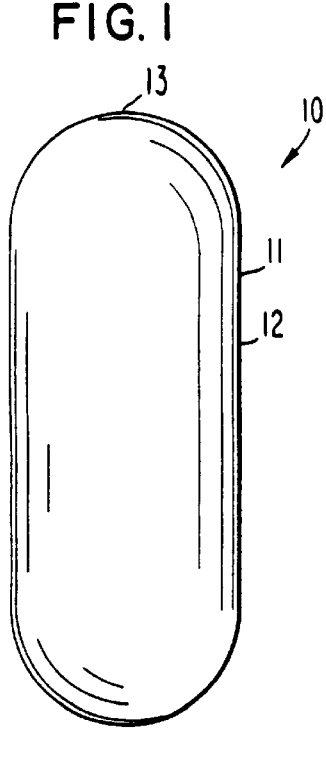
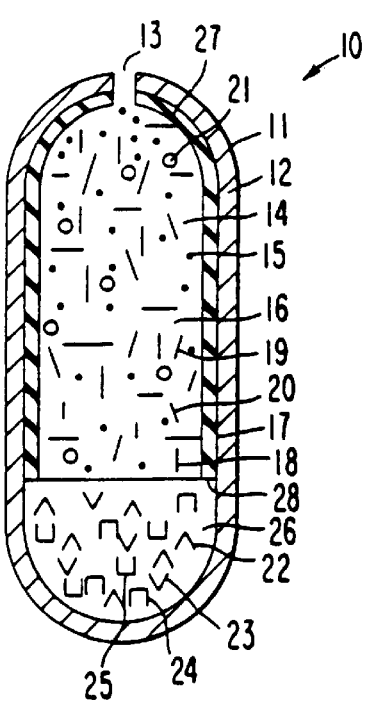
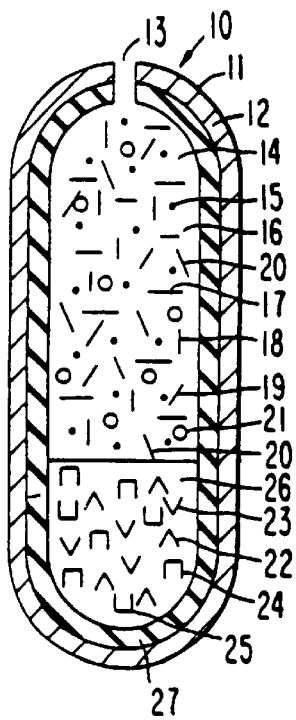
FIG. 4
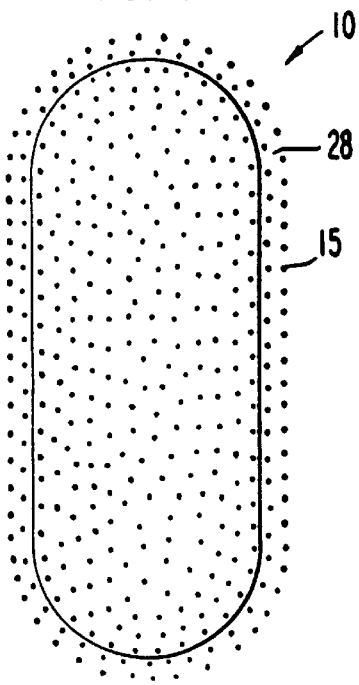
FIG. 5
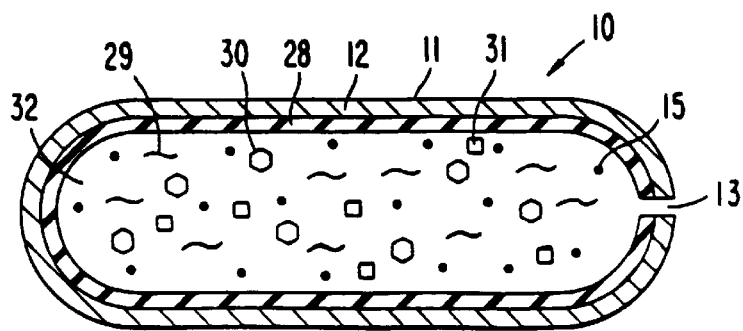

EFFECTIVE THERAPY FOR EPILEPSIES

This application is a division of application U.S. Ser. No. 08/439,915, filed May 12, 1995, now abandoned which application Ser. No. 08/439,915 is a continuation application of U.S. Ser. No. 08/234,092 filed Apr. 28, 1994, and benefit of the filing date of said earlier filed application is claimed under 35 USC § 120.

FIELD OF THE INVENTION

This invention pertains of novel and unobvious dosage forms for administering a drug effective in the therapy of the epilepsies. The invention concerns also a pharmaceutical composition comprising an antiepileptic drug and a pharmaceutical carrier. The invention relates further to the manufacture of a dosage form for administering a drug useful for treating epilepsies. Additionally the invention pertains to a method for producing antiepileptic therapy in a patient in need of antiepileptic therapy.

BACKGROUND OF THE INVENTION

The term epilepsies is a collective designation for a group of central nervous system disorders having in common the repeated occurrence of sudden and transitory episodes of abnormal phenomena of motor, convulsion, sensory, autonomic, or psychic origin. The seizures are nearly always correlated with abnormal and excessive discharges in the brain which can be recorded by an electroencephalogram.

Epilepsy afflicts millions of people worldwide, and the disease is more common in children than in adults. For the purposes of drug treatment, it is useful to classify patients according to the type of seizure the patient experiences. The generally accepted classification of epileptic seizures comprises partial seizures consisting of focal and local seizures, and generalized seizures consisting of convulsive of non-convulsive seizures. Partial seizures are classified further as simple partial seizures, complex partial seizures, and partial seizures secondarily generalized. Generalized seizures are classified further as absence seizures, atypical absence seizures, myoclonia seizures, clonic seizures, tonic seizures, tonic-clonic and atonic seizures. The epilepsies are presented in *The Pharmacological Basis of Therapeutics*, 8th Ed. Chapter 19 (1990). Editors Gilman and Rall, Pergamon Press.

Antiepileptic drugs are available for treating epilepsies, as disclosed in *Pharmaceutical Sciences*, Remington's, 18Ed., pp 1072–1081 (1990) published by Mack Publishing Co., and while the drugs are useful for treating the epilepsies, there are many shortcomings associated with these drugs. For instance, the drugs often are poorly soluble in aqueous and biological fluids, which property makes it difficult to both provide and dispense the drugs from a dosage form in a known dose over and extended time. The drugs also can be extremely hygroscopic and they may liquify rapidly, which physical-chemical characteristic dictates against their delivery from a dosage form at a controlled rate over a prolonged period of time. Then too, many drugs exhibit a short half-life that can lead to fluctuations in blood antiepileptic drug levels. These properties can interfere with manufacture and the release of the drugs from dosage form and from pharmaceutical compositions; and these shortcomings are serious drawbacks in the management of epilepsies.

Prior to this invention, the prior art administered an antiepileptic drug in conventional forms like a standard nonrate tablet or a common dose-dumping capsule at repetitive dosing intervals. The prior art modes of therapy leads to a drug concentration in the blood during the dosing interval, followed by a decrease in drug concentration as a result of drug absorption, distribution, metabolism, and elimination. The concentration difference in dosing intervals is related to the presence and to the absence of administered drug, which is a major disadvantage associated with conventional dosage forms. Conventional dosage forms and their mode of operation are discussed in *Pharmaceutical Sciences*, Remington, 18th Ed., pp 1676–1686 (1990), Mack Publishing Co.; *The Pharmacological and Clinical Pharmacokinetics*, 3rd Ed., pp 1–28 (1984), published by Lea & Febiger, Philadelphia, Pa.; and U.S. Pat. Nos. 3,598,122 and 2,598,123, both issued to Zaffaroni.

The above presentation dictates of the critical need for a dosage form that overcomes the shortcomings of conventional dosage forms, including tablets, capsules, elixirs and suspensions. These conventional dosage forms produce peaks and valley patterns, and they do not provide for dosage-regulated drug therapy over an extended period of time. The drug, as delivered by the prior art is dosed twice of thrice a day, which does not lend itself to controlled and sustained therapy. This prior art pattern of drug administration speaks of the need for a dosage form that can administer the drug in a rate-controlled pattern over an extended time to provide constant therapy and thereby eliminate the peaks and valleys and eliminate the need for multiple uncontrolled dosing of the drug.

The prior art provided controlled-release dosage forms that can administer a drug continuously over time for controlled-rate therapy, as in, for example, U.S. Pat. No. 4,327,725 issued to Cortese and Theeuwes, and in U.S. Pat. Nos. 4,612,008; 4,765,989; and 4,783,337 issued to Wong, Barclay, Deters and Theeuwes. The dosage forms disclosed in these patents provide a controlled-rate drug delivery over an extended time to provide constant drug therapy and thereby eliminate the need for multiple dosing of the drug. These dosage forms can deliver many drugs for their intended therapy, but there are certain drugs that are not readily manufactured and delivered from dosage forms. For example, phenytoin sodium converts to practically insoluble phenytoin in the gastrointestinal pH range of 1 to 8 and the release of unprotected drug in this range is incomplete and this abstracts from acceptable therapy.

It is immediately apparent, in the light of the above presentation, that an urgent need exists for a dosage form endowed with controlled-release delivery for the administration of an antiepileptic drug for antiepileptic therapy. The need exists for this dosage form for delivering an antiepileptic drug in a controlled-sustained dose in a therapeutic antiepileptic range and for simulateously providing extended therapy. It will appreciated by those versed in the dispensing antiepileptic drug art, that such a dosage form that can administer an antiepileptic drug in a controlled-rate dose over time, and it would be a major advancement in the therapy of the epilepsies.

DISCLOSURE OF OBJECTS OF THE INVENTION

Accordingly, in view of the above presentation, it is an immediate object of this invention to provide a dosage form for delivering an antiepileptic drug for treating epilepsies that overcomes the shortcomings known to the prior art.

Another object of the present invention is to provide a dosage forms that delivers an antiepileptic drug in a continuous-release dose over time.

Another object of the present invention is to provide a dosage form for administering an antiepileptic drug as a controlled-rate in a therapeutic-dose over an extended period of time.

Another object of the present invention is to provide a dosage form that delivers an antiepileptic drug in the gastrointestinal tract, by a process selected from osmotic, duffusion, bioerosion, or ion-exchanged kinetics.

Another object of the invention is to provide an antiepileptic drug formulation in a controlled-continuous-release dose to a patient for maintaining an essentially constant antiepileptic level in the blood as a function of a prolonged-release system.

Another object of the invention is to provide an antiepileptic continuous-release dosage form that provides a slow-release of an antiepileptic formulation over an extended time.

Another object of the invention is to provide a dosage form that substantially reduces and/or substantially eliminates the unwanted influences of a gastrointestinal environment on the delivery of an antiepileptic formulation in the gastrointestinal tract.

Another object of the present invention is to provide an improvement in a dosage form that administers an antiepileptic drug formulation, wherein the improvement comprises delivering the antiepileptic drug formulation in a continuous-release dose form the dosage form for predictable and improved therapy.

Another object of the invention is to provide a dosage form that delivers an antiepileptic drug formulation orally to a patient in need of antiepileptic therapy.

Another object of the present invention is to provide both a fast-release prompt delivery and a slow-release extended antiepileptic drug formulation from a single dosage form comprising a first and a second antiepileptic drug formulation for administering to a patient experiencing epilepsies.

Another object of the present invention is to provide a method for the prevention and for the control of epileptic seizures.

Another object of the present invention is to provide a method of add-on antiepileptic drug therapy for patients taking other epilepsy medication, thereby providing adjunctive therapy in epilepsy patients.

Another object of the present invention is to provide a dosage form that delivers by a process selected from the group consisting of osmotic, diffusion, bioerosion and ion-exchange a therapeutic dose of an antiepileptic drug formulation over an extended time for dosage form governed antiepileptic therapy.

Another object of the invention is to provide a method for administering an antiepileptic drug by orally administering the antiepileptic drug in a dose per unit time over an extended time to a patient in need of antiepileptic therapy.

Another object of the present invention is to provide a method for administering an antiepileptic drug formulation in a therapeutic range while simultaneously-avoiding a toxic range of the antiepileptic drug formulation.

Another object of the invention is to provide a method for administering an antiepileptic drug formulation by administering a dosage form that administers by osmotic, diffusion, bioerosion, or ion-exchange an antiepileptic drug formulation as a dosage form governed rate over an extended time.

Another object of the present invention is to provide a therapeutic composition comprising an antiepileptic drug blended with an antiepileptic pharmaceutically acceptable carrier.

Another object of the invention is to provide a dosage form comprising an antiepileptic drug formulation, which dosage form passes the pharmacokinetic property for delivering substantially 100% of the antiepileptic drug formulation in a programmable and controlled manner therby substantially avoiding inherent drug residual in the dosage form.

Another object of the invention is to provide a laminate comprising a first lamina comprising an antiepileptic drug formulation and a second lamina initially-free of an antiepileptic drug formulation.

Another object of the present invention is to provide a dosage form for buccally or sublingually administering an antiepileptic drug.

Other objects, features and advantages of the invention will be more apparent to those versed in the dispensing art from the accompanying detailed specification, taken in conjunction with the drawings and the claims.

BRIEF DESCRIPTION OF THE DRAWINGS

In the drawing figures, which are not drawn to scale, but one set forth to illustrate various embodiments of the invention, the drawing figures are as follows:

Drawing FIG. 1 is a general view of a dosage form designed and shaped for oral administration of a drug for the therapy of epilepsies at a continuous-release rate over time to a patient in need of therapy for the management of epilepsies;

Drawing FIG. 2 is an opened view of drawing FIG. 1 for depicting an embodiment of the dosage form comprising a pharmaceutical comprising a drug indicated for the management of epilepsies and a composition comprising means for pushing the pharmaceutical composition from the dosage form;

Drawing FIG. 3 is an opened view of drawing FIG. 1 for depicting an embodiment of the dosage form comprising an internal subcoat positioned between the internal surface of the wall of the dosage form and the pharmaceutical composition and the composition for pushing the pharmaceutical composition from the dosage form;

Drawing FIG. 4 is a view of a dosage from provided by the invention, which dosage form comprises a prompt-release coat comparison, a drug for the therapy of the epilepsies on the exterior surface of the dosage form;

Drawing FIG. 5 is an opened view of a dosage form provided by the invention, which dosage form comprises a single composition in the dosage form comprising a drug for treating epilepsies and means for delivering the single composition from the dosage form;

Drawing

Drawing

Drawing

Drawing

In the drawing figures and in the specification, like parts in related drawing figures are identified by like numbers. The terms appearing earlier in the specification and in the description of the drawing figures, as well as embodiments thereof, are further described elsewhere in the specification.

DETAILED DESCRIPTION OF THE DRAWING

Figure 10:
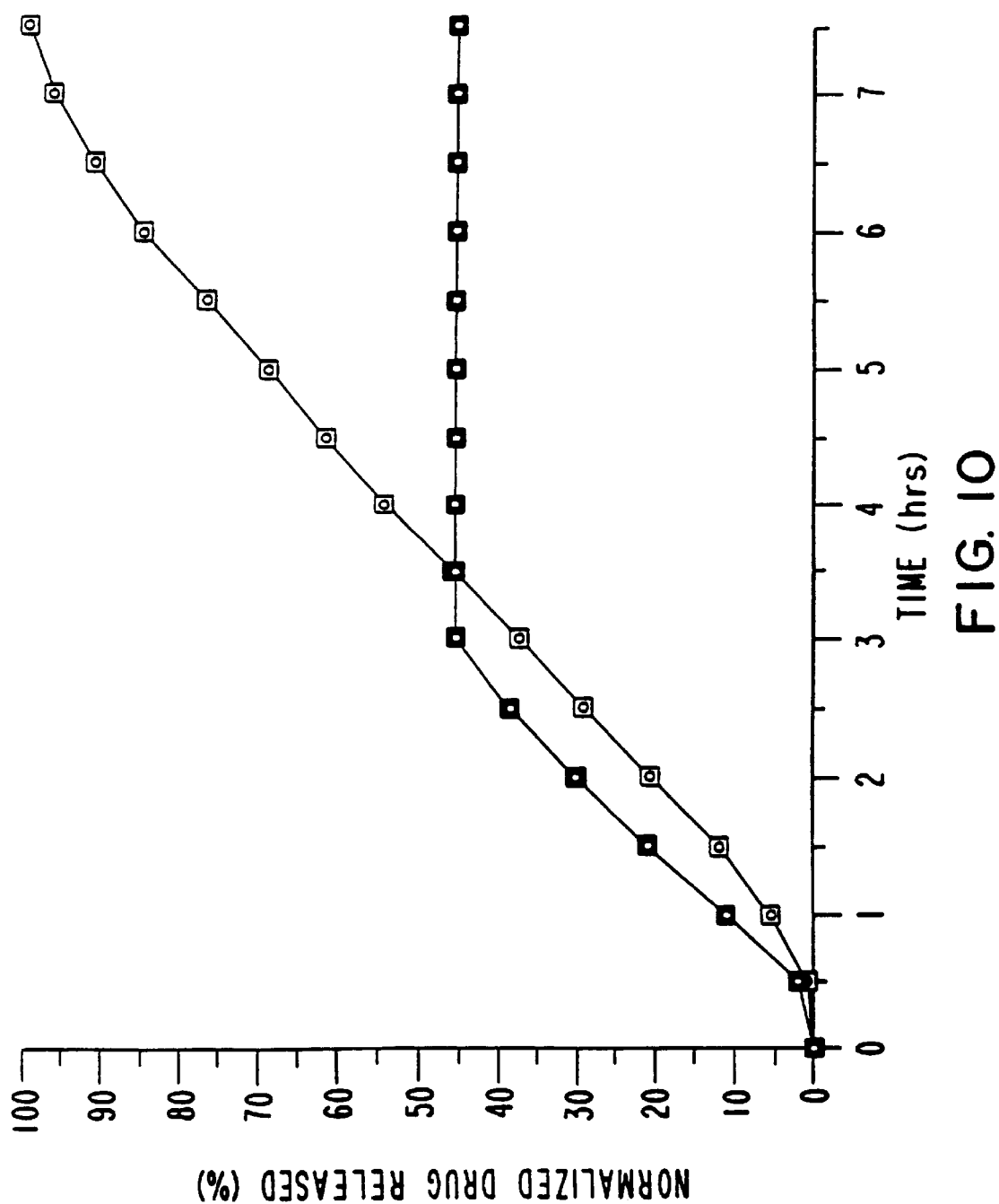
FIG. 10 illustrates the internal coat protects cracking in an external wall.

Turning now to the drawing figures in detail, which drawing figures are examples of dosage forms provided by this invention and which examples are not to be construed as limiting, one example of a dosage form is seen in drawing FIG. 1. In drawing FIG. 1, a dosage form 10 is seen comprised of a body member 11, which body member 11 comprises a wall 12, that surrounds and forms an internal area, not seen in drawing FIG. 1. Drawing FIG. 10 comprises at least one exit 13 that connects the exterior of dosage form 10 with the interior of dosage form 10. The dosage form 10 of drawing FIG. 1 illustrates a controlled-release dosage form that delivers an antiepileptic drug over an extended time. The dosage form comprises controlled-release properties provided by this invention is successful at maintaining substantially therapeutic antiepileptic levels in the blood or in body tissue. The dosage form, as seen in drawing FIG. 1, embraces the shape of a vertically model tablet manufactured as a dosage form, comprises continuous-release, extended release and prolonged-release forms. These dosage forms provide antiepileptic blood levels and targeted tissue levels within a therapeutic range optionally below side-effect levels over time. An extended period of time, as used for the purpose of this invention includes a prolonged period of time, and a continuous-controlled release period of time. The extended, prolonged and continuous time denotes a duration of antiepileptic drug deliver time over that achieved by conventional delivery forms such as noncontrolled tablets and noncontrolled capsules.

In drawing FIG. 2, dosage form 10 as seen in opened section. In drawing FIG. 2, dosage form 10 comprises a body 11, a wall 12 that surrounds and defines an internal compartment 14. Internal compartment 14 communicates through exit port 13 with the exterior of dosage form 10. Wall 12 of dosage form 10 comprises totally or in a least a part a composition that is permeable to the passage of an exterior fluid, such as an aqueous fluid or a biological fluid present in the gastrointestinal tract. Wall 12 is nontoxic and it is substantially impermeable to the passage of an antiepileptic drug 15, represented by dots, present in lumen-compartment 14. Wall 12 substantially inert, and it maintains its physical and chemical integrity during the dispensing life of antiepileptic drug 15. The phase, maintains its physical and chemical integrity means wall 12 does not lose its structure and it does not undergo chemical change during the dispensing of antiepileptic drug 15. In drawing FIG. 2, dosage form 10 comprises means 27 for providing protection for antiepileptic drug 15 from the pH of 1 to 8 of the gastrointestinal environment, thereby providing means 27 for ensuring antiepileptic drug 15 can give its full therapeutic benefit to an epileptic patient. Means 27, also gives support as a sibocat to external wall 12 to give wall 12 support against the stress and the strain of a fluid moving gastrointestinal tract. Means 27 comprises a nonionic, nontoxic fluid pervious polymer. In drawings FIG. 2, means 27 surrounds the internal area of compartment 14 housing drug 15. An exit passageway 13 in means 27 is present to enable the delivery of drug 15 from dosage form 10. An opening 28 in means 27 distant from exit passageway 13 is an internal channel for an expandable layer 26 to move towards exit passageway 13 contributing in the delivery of drug 15 from dosage form 10.

Wall 12 comprises a composition that does not adversely effect an animal, a human, or components of the dosage form. Compositions for forming wall 12, are in one embodiment, comprises a member selected from the group consisting of a cellulose ester polymer, a cellulose ether polymer, and a cellulose ester-ether polymer. These cellulosic polymers have a degree of substitution, D.S. on the anhydroglucose unit, from greater than 0 up to 3 inclusive. By degree of substitution is meant the average number of hydroxyl group originally present on the anyhydroglucose unit comprising the cellulose polymer that are replaced by a substituting group. Representative wall 12 polymers comprise a member selected from the group consisting of cellulose acylate, cellulose diacylate, cellulose triacylate, cellulose acetate, cellulose diacetate, cellulose triacetate, mono-, di- and tricellulose alkanylates, mono-, di-, and tricellulose aroylates, mono-, di-, and tricellulose alkylinates, and mono-, di-, and tricellulose alkinylates. Exemplary polymers include cellulose acetate having a D.S. up to 1 and an acetyl content up to 21%; cellulose acetate having a D.S. of 1 to 2 and an acetyl content of 21 to 35%; cellulose acetate having a D.S. of 2 to 3 and an acetyl content of 35 to 44.8%, and the like. More specific cellulosic polymers comprise cellulose propionate having a D.S. of 1.8 and a propyl content of 39.2 to 45% and a hydroxyl content of 2.8 to 5.4 cellulose acetate butyrate having a D.S. of 1.8, an acetyl content of 13 to 15% and a butynyl content of 34 to 39%; cellulose acetate butyrate having an acetyl content of 2 to 29%, a butyryl content of 17 to 53% and a hydroxyl content of 0.5 to 4.7; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulos dipentanoate, co-esters of cellulose such as cellulose a acetate butyrate, and cellulose acetate propionate.

Additional semipermeable polymers comprise acetaldehyde dimethylcellulose acetate, cellulose acetae ethylacarbamate, cellulose acetate methylcarbamate, cellulose diacetate propylcarbamate, cellulose acetate diethylaminoacetate, semipermeable polyamide; semipermeable polyurethane; semipermeable sulfonated polystyrene; semipermeable cross-linked selective polymer formed by the coprecipitation of a polyanion and polycation as disclosed in U.S. Pat. Nos. 3,173,876; 3,276,586; 3,541,005; 3,541,006; 3,546,142; semipermeable polymers as disclosed by Loeb and Sourirajan in U.S. Pat. No. 3,133,132; semipermeable lightly cross-linked polystyrenes; semipermeable cross-linked poly(sodium styrene sulfonate); semipermeable cross-linked poly(vinylbenzyltrimethyl ammonium chloride); semipermeable polymers possessing a fluid permeability of $2.5 \times 10^{-8}$ to $2.5 \times^{-4}$ (cm$^2$/hr·atm) expressed per atmosphere of hydrostatic or osmotic pressure difference across the semipermeable wall. The polymers are known to the polymer art in U.S. Pat. Nos. 3,845,770; 3,845,770; and 4,160,020; and in *Handbook of Common Polymers* by Scott, J. R. and Roff W. J., 1971, published by CRC Press; Cleveland, Ohio.

Compartment 14 comprises a drug 15 effective in the therapy of the epilepsies. The antiepileptic drug 15 comprises a member selected from the group consisting of hydantoins, barbiturates, deoxybarbiturates, iminostilbenes, succinimemdes, oxazolidinediones, and benzodiazepines. The antiepileptic drug 15 for treating all types of epilepsy comprise a member selected from the drug consisting of phenytoin, phenytoin sodium, phenytoin potassium, mephenytoin, ethytoin, pehnobarbital, phenobarbital sodium, phenobarbital potassium, primidone, carbamazepine, ethosuximide, methsuximide, phensuximide, trimexhadione, clonazepam, clorazepate, phenacemide, paramethadione, primaclone, clobazam, felbamate, flunarizine, lamotrigine, progabide, vigabatrin, eterobarb, gabagpentin, excarbazepine, ralitone, tiagabine, sulthiame, and tioridone. The antiepileptic drug 15 are disclosed in *Pharmaceutical Sciences*, by Remington, 18th Ed., pp 1072–1081 (1990), Mark Publishing Co., Easton, Pa; and *The Pharmacological Basis of Therapeutics*, by Gilman and Rall, 8th Ed., pp 436–462 (1990), Pergamon Press, New York, N.Y. The dosage amount of antiepileptic drug 15 is 10 nanograms (ng) to 2000 milligrams (mg) that is delivered over an extended period of 30 hours. The antiepileptic drug 15 is present in individual doses of 5, 30, 50, 75, 100, 130, 150, 200, 250, 300, 350, 400, 500, 625, 700, 1000 to 2000 mgs of antiepileptic drug 15. The antiepileptic drug 15 is delivered by dosage form 10 over a period of immediate delivery of time up to 30 hours. The antiepileptic drug 15 can be administered for adjunctive therapy with a different antiepileptic drug 15 in epilepsy patients. Representative of adjunctive antiepileptic drugs 15 that can be administered from dosage form 10 comprise phenytoin and phenobarbitone, phenytoin and carbamazepine; phenytoin and primidone, phenobarbitone and carbamazepine, carbamazepine and primidone, felbamate and phenytoin, felbamate and carbamazepine, felbamate and gabapentin, phenytoin and gabapentin, and carbamazepine and gabapentin. The dosage amount of adjunctive-antiepileptic drug 15 for each adjunctive drug 15 is 10 ng to 1000 mg with the total dosage for the adjunctive pain is 10 ng to 2000 mg.

Antiepileptic drug 15 is present in compartment 14 in antiepileptic drug 15 formulation 16. The antiepileptic drug 15 formulation 16 comprises 0.5 wt % to 90 wt % of antiepileptic drug 15, a drug which dispensing polymer is compatible with antiepileptic drug 15 and aids in delivering antiepileptic drug 15 in a known dose from dosage form 10. Dispensing polymer 17 comprises a member selected from the group consisting of an osmopolymer possessing a 15,000 to 4,500,000 molecular weight, a polyalkylene oxide possessing a 175,000 to 225,000 molecular weight, a polyalkylene oxide possessing a 275,000 to 325,000 molecular weight, and a carboxyalkylcellulose possessing a 15,000 to 175,000 molecular weight. Representative members comprise a polyethylene oxide of 200,000 molecular weight, a polyethylene oxide of 300,000 molecular weight and an alkali including sodium and potassium carboxymethylcellulose of 40,000 to 1000,000 molecular weight, as represented by dashes 17. Layer 16 comprises additionally 0 wt % to 20 wt % of an osmotically effective solute also known as an osmagent 18 for contributing to the delivery kinetics of antiepileptic drug 15. Representative if osmagent 18, represented by vertical dashes 18, comprises a member selected from the group consisting of magnesium sulfate, magnesium chloride, sodium chloride, potassium chloride, lithium chloride, potassium sulfate, sodium sulfate, mannitol, sorbitol, inositol, urea, sucrose, glucose, glucitol, polyhydride alcohol and osmagents exhibiting an osmotic pressure gradient across semipermeable wall 12 of 5 atmospheres to 500 atmospheres. Layer 16 comprises 0.1 wt % to 25 wt % of a polyvinyl pyrrolidone of 5,000 to 150,000 as a suspending and hydropumping agent, represented by slanted lines 19; 0 wt % to 5 wt % of a lubricant 20 selected from the group consisting of sodium stearate, magnesium stearate, stearic acid, calcium stearate, calcium oleate, oleic acid and caprylic acid as represented by dashes 20; and 0 wt % to 10 wt % of a surfactant 21 as represented by a nonionic surfactant to prevent sticking to the wall of the dosage form, as represented by polyethylene glycol stearate, propylene glycol monolaurate, polyethylene glycol sorbitol, and polyethylene glycol sorbitol lanolin. The total weight of all ingredients in layer 16 is equal to 100 wt %, wherein wt % denotes weight percent.

Compartment 14 comprises an expandable layer 26 that cooperates with antiepileptic drug layer 16 to deliver antiepileptic drug 15 from dosage form 10. Expandable layer 26 comprises 30 wt % to 70 wt % of an expandable polymer 22 as represented by a polyalkylene oxide comprising a 3,000,000 to 7,500,000 molecular weight, which is a different polyalkylene oxide than the polyalkylene oxide in an antiepileptic drug layer 16, a carboxyalkylcellulose comprising a 250,000 to 3,250,000 molecular weight that is a different carboxyalkylcellulose than the carboxyalkylcellulose in layer 16; 5 wt % to 50 wt % of an osmagent 23; 0 wt % to 25 wt % of a hydroxypropyl alkylcellulose 24 possessing a 9,000 to 375,000 molecular weight; 0 wt % to 3 wt % of ferric oxide; 0 wt % of a lubricant; and 0 wt % to 15 wt % of a hydroxyalkylcellulose 25 comprising a 7,000 to 250,000. Representative of a polyalkylene oxide is polyethylene oxide; representative of hydroxypropylalkylcellulose are hydroxypropylmethylcellulose, hydroxypropylethylcellulose, hydroxypropylisopropylcellulose, hydroxypropylbutylcellulose and hydroxpropylpentylcellulose; representatives of an oxmagent comprise a member selected from the group consisting of an inorganic salt, organic salt, acid, ester, ether, carbohydrate, oxide, magnesium sulfate, magnesium chloride, sodium chloride, lithium chloride, potassium chloride, potassium sulfate, sodium sulfate, sodium sulfite, lithium sulfate, potassium lactate, mannitol, urea, magnesium succinate, tartaric acid, raffinose, sorbitol, sucrose, fructose, and glucose; representative of lubricant comprise a member selected from the group consisting of stearic acid, magnesium stearate, calcium stearate, magnesium oleate, calcium oleate, oleic acid, caprylic acid, magnesium palmitate, and calcium lactate; and representative of carboxyalkylcellulose comprise a member selected from the group consisting of alkalcarboxyalkylcellulose, sodium carboxymethyl-cellulose, potassium carboxymethylcellulose and sodium carboxyethylcellulose. The total weight of all ingredients in the expandable layer 26 is equal to 100 wt %.

Dosage form 10 as seen in drawing FIG. 3 dispicts another dosage form provided by this invention. Dosage form 10 comprises an exterior wall 12, internal compartment 14 comprising antiepileptic drug 15, in antiepileptic drug 15 formulation 16, osmopolymer 17, osmagent 18, polyvinylpyrrolidone, 19, lubricant 20 and surfactant 21; and expandable layer 26 comprising expandable polymer 22, osmagent 23, hydroxypropylalkylcellulose 24 and hydroxyalkylcellulose 25. Dosage form 10 of drawing FIG. 3 comprises further an interior wall 27, which interior wall 27 is in contracting relation with exterior wall 12, antiepileptic drug formulation 16 and expandable formulation 26. Interior wall 27 is positioned between wall 12 and antiepileptic drug formulation 16 and expandable formulation 26 and it surrounds antiepileptic drug formulation 16 and expandable formulation 26, except for exit orifice 13. The dual walls 12 and 27 provides unexpected advantages as wall 12 and wall 27 in combination protect a hydroscopic antiepileptic drug 15 from the unwanted influences of aqueous and biological fluids, they shield an antiepileptic drug 15 from converting from a soluble to an insoluble antiepileptic drug 15 in the gastrointestinal pH range of 1 to 8. The combination of wall 12 and wall 27 provides for both fast-release and slow-release of antiepileptic drug 15. A fast-release of antiepileptic drug 15 can be effected by providing wall 12 thinner than wall 27. A thin wall 12 lets an increased fluid flux through wall 12 thereby providing a greater volume in compartment 14 for aiding in delivery of antiepileptic drug 15 from dosage form 10. A slow-release of antiepileptic drug 15 is effected by providing wall 12 thicker that wall 27, as a thicker wall restricts the flux into compartment 14. The presence of wall 27 provides structural support for wall 12. In providing support for wall 12, wall 27 substantially prevents and/or lessens the incidence of cracking of wall 12. Wall 27 also in cooperation with wall 12 substantially maintains the integrity and the performance of dosage form 10.

Dosage form 10, as seen in drawing FIG. 4, depicts another manufactured provided by invention. Dosage form 10 comprises an external coat 28 on the exterior surface of dosage form 10. Exterior coat 28 is a therapeutic composition comprising a member selected from the group consisting of alkyl cellulose, methyl cellulose, hydroxyalkylcellulose, hydroxypropylcellulose, hydroxypropylmethyl-cellulose, hydroxypropylethylcellulose, and acacia. External coat 28 optionally comprises 0 to 5 wt % of polyethylene glycol, or 0 to 5 wt % acetylated triglyceride. Coat 28 provides antiepileptic drug 15 therapy immediately as coat 28 dissolves or undergoes dissolution in the presence of gastrointestinal fluid and concurrently therewith delivers antiepileptic drug 15 to an antiepileptic drug 15 receiving patient. Coat 28 provides antiepileptic drug 15 on entrance into the gastrointestinal tract for immediate antiepileptic drug 15 therapy.

In drawing FIG. 5, dosage from 10 is seen in opened view. In drawing FIG. 5, dosage form 10 comprises body 11, wall 12, wall 27, exit port 13 and internal compartment 14 as identified in previous drawing FIGS. 2 and 3. Internal compartment 14 comprises a single homogenous composition comprising 0.5 wt to 80 wt % of antiepileptic drug 15; from 5 wt % to 50 wt % of a polyethylene oxide comprising a 150,000 to 725,000 molecular weight; from 0 wt % to 40 wt % of a cellulose either 29 selected from the group consisting of hydroxypropylalkycellulose, hydroxypropymethyl-cellulose, hydroxpropylethylcellulose, hydroxypropylisopropylcellulose, hydroxypropylbutylecellulose, hydroxypropylpentylcellulose, and hydroxypropylhexylcellulose possessing a 9,000 to 240,000 molecular weight; 0 wt % to 20 wt % of an osmotically effective solute 30 selected from the group consisting of an inorganic salt, an organic salt, acid, ester, carbohydrate, oxide, and osmotically effective solutes that exhibit an osmotic pressure gradient across wall 12; and 0 wt % to 3.5 wt % of lubricant 31. The total weight of all ingredients in single core 32 is equal to 100 wt %.

The antiepileptic drug 15 selected from the group consisting of hydantoins, barbiturates, deoxybarbiturates, iminostilbenes, succinimides, oxazolidinediones and benzodiazepines for the purpose of this invention can be administered from a dosage form selected from the group consisting of bioerodible dosage form, diffusion dosage form, and ion-exchanged dosage forms.

The bioerodible dosage form 10 comprises a bioerodible polymer matrix comprising 1 mg to 1200 mg of an antiepileptic drug selected from the group consisting of phenytoin, phenytoin sodium, phenytoin potassium, mephenytoin, ethotin, phenobarbital, phenobarbital sodium, phenobarbital potassium, primidone, carbamazepine, ethosuximide, methsuximide, phensuximide, trimethadione, clonazepam, clorazepate, phenacemide, paramethadione, primaclone, clobazam, felbamate, flunariizine, lamotrigine, progabide, vigabatin, eterobarb, gabapentin, oxcarbazepine, ralitoline, tiagabine, sulthiame and tioridone in 1 mg to 1200 mg of a polymer matrix that delivers the said drug to a drug receptor at a rate release controlled by the bioeroding polymer matrix thirty minutes to seven days. The bioerodible polymers for forming the dosage form containing the antiepileptic drug include a member selected from the group consisting of poly(ester). poly (amine), poly(lacitde), poly(glycolide), poly(lactide-co-glycolide), poly(caprolactone), poly (hydroxybutyric acid), poly(orthoester), poly (orthocarbonate), poly(acetate), poly(carbohydrate), poly (peptide), poly(acetal) and poly(dihydropyron).

The diffusion-dosage form that release a drug under the influence of fluid flux mechanism comprise a membrane-controlled diffusion consisting of diffusion through a non-porous polymer membrane or through a porous-polymer membrane. The diffusion-operated dosage form structurally includes a polymer matrix with an antiepileptic drug therein, that is released by the process of diffusion and, a reservoir or depot of an antiepileptic drug therein that is released therefrom by the process of diffusion through a contacting polymer rate-governing membrane. Representative diffusional polymers for providing a differsional-dosage form comprising 1 mg to 1200 mg of antiepileptic drug with 1 mg to 1200 mg of a polymer selected from the group consisting of a poly(olefin), poly(vinyl), poly(carbohydrate), poly (peptide), poly(additon), poly(conden-sation), poly(rubber) and poly(silicone) polymers. Representative of specific polymers are a member selected from this group consisting of poly(ethylene), poly(propylene), copoly(ethylenevinyl acetate), poly(isobutylene), poly(isobutylethylene), poly (vinylacetate), cross-linked poly(vinyl alcohol), poly (methacrylate), poly(amide), poly(ester), and poly(silicone).

Dosage form 10 comprising an antiepileptic drug 15 can be manufactured as an ion-exchange dosage form 10 which comprises a water-insoluble cross-linked polymers with an antiepileptic drug bound to an ion-exchange resin. In dosage form 10, an antiepileptic drug 15 is released at a rate controlled by the antiepileptic drug 15 resin complex by the ionic environment within the gastrointestinal tract. The antiepileptic drug 15 attached to the resins are released at a rate controlled by the exchanging-rate with charged ion in the gastrointestinal tract. This ion-exchange dosage form 10 comprises cation-exchange resins containing electronegative charges and anion-exchange resins containing electropositive charges. This cation-exchange resins include strong-acid or weak-acid resins as with sulfonic acid, carboxylic acid, and phosphoric acid; and the anion-exchange resins include strong-base and weak-base resins with quaternary ammonium, secondary amine, tertiary amine, aromatic and tertiary amine aliphate resins. Examples include acidic ion-exchange resins such as Amberlite IR-120, basic ion-exchange resins such as Amberlite IR-400, and weak basic ion-exchange resins such as Amberlite IR-45.

Dosage form 10, as further provided by this invention, and as seen in the above drawing figures can be manufactured for administering an antiepileptic drug 15 by oral route. Dosage form 10 comprising exterior and interior antiepileptic drug 15 can be sized and shaped for administering antiepileptic drug 15 by the sublingual or the buccal routes. The sublingual and buccal routes can be used for quicker therapy and they can be used when a small dose of antiepileptic drug 15 is needed for therapy. The buccal and sublingual routes can be used as a by-pass of the first pass of hepatic metabolism antiepileptic drug 15. The sublingual or buccal routes can be used for administering the first dose of antiepileptic drug 15 followed by permitting dosage form 10 entrance into the gastrointestinal tract for antiepileptic 15 delivery.

Process of Providing the Dosage Form

Dosage form 10, when manufactured as an osmotic controlled-release dosage form comprises at least one passageway 13. The phrase controlled-release as used herein, indicates that control is exercised over both the duration and the profile of the antiepileptic-release pattern. The expression passageway, as used for the purpose of this invention, includes aperture, orifice, bore, pore, porous element through which the antiepileptic drug 15 can be pumped, diffuse, travel or migrate a hollow fiber capillary tube, porous overlay, porous insert, microporous member, and porous composition. The expression also includes a compound that erodes or is leached from wall 12 in the fluid environment of use to produce at least one passageway 13 in dosage form 10. Representative compounds suitable for forming at least one passageway, or a multiplicity of passageways, includes an erodible poly(glycolic) acid or poly(lactic) acid member in the wall; a gelatinous filament; a water-removable poly(vinyl) alcohol); leachable compounds such as fluid removable pore-forming polysaccharides, acid, salts, or oxides. A passageway or a plurality of passageways can be formed by leaching a compound such as sorbitol, surcrose, lactose, maltose, fructose, or the like, from wall 12 to provide a controlled-release dimensioned pore-passageway. The passageway can have any shape such as round, triangular, square, elliptical, and the like, for assisting in the controlled-metered release of antiepileptic drug 15 from dosage form 10. Dosage form 10 can be constructed with one or more passageways in spaced apart relation to one or more surfaces of a dosage form 10. Passageway 13 and equipment for forming passageways are disclosed in U.S. Pat. Nos. 3,845,770 and 3,916,899 by Theeuwes and Higuchi; in U.S. Pat. No. 4,063,064 by Saunders et al; and in U.S. Pat. No. 4,088,864 by Theeuwes et al. Passageways comprising controlled releasing dimension, sized, shaped and adapted as a releasing-pore formed by aqueous leaching to provided a releasing-pore of controlled release-rate are disclosed in U.S. Pat. No. 4,200,098 by Ayer and Theeuwes; and in U.S. Pat. No. 4,285,987 by Ayer and Theeuwes.

Wall 12 is manufactured in one process, comprises an air suspension process. This procedure consists in suspending and tumbling a compressed drug core comprising a single layer or a bilayer core, in a current of air and wall forming composition until a wall is applied to the drug-core or the drug-push compartment. The air suspension procedure is well-suited for independently forming the wall. The air suspension procedure is described in U.S. Pat. No. 2,799,241; *J Amer Pharm Assoc*, Vol 48, pp 451–454 (1959); and ibid, Vol 49, pp 82–84 (1960). Dosage form 10 can be coated also with a wall-forming composition in a Wurster® air suspension coater, using methylene dichloride-methanol cosolvent, for example, 80:20, wt:wt, an ethanol-water, or acetone-water cosolvent, for example, 95:5 wt:wt using 2.5 to 4% solids. An Aeromatic® air suspension coater using a methylene dichloride-methanol cosolvent for example, 80:20 wt:wt, can be used for applying wall 12. Other wall forming techniques such as a pan-coating system, wherein wall forming compositions are deposited by successive spraying of the composition on the drug-core or drug bilayer to provide a compartment, accompanied by tumbling in a rotating pan. Finally, the wall coated compartments are dried in a forced air over at 30° C. to 50° C. for up to a week to free dosage form 10 of solvent. Generally, the wall formed by these techniques have a thickness of 1 to 30 mils (0.0254 mm to 0.762 mm).

Dosage form 10 of the invention is manufactured by standard manufacturing techniques. For example, in one manufacture the drug and other core-forming ingredients comprising a single drug layer or bilayer core with drug facing the exit means 13 are blended and pressed into a solid layer, or a solid bilayer. The drug and other ingredients can be dry-blend or blended with a solvent and mixed into a solid or semisolid formed by conventional methods such as ball-milling, calendaring, stirring, roll-milling or churning and then pressed into a preselected shape. The layer possesses dimensions that correspond to the internal dimensions of the area the layer is to occupy in the dosage form and in a bilayer it also possesses dimensions corresponding to the second layer for forming a contacting arrangement therewith. Next, in a bilayer core, the push layer is placed in contact with the drug layer. The push layer is manufactured using techniques for providing the drug layer. The layering of the drug layer and the push layer can be fabricated by convention press-layering techniques. Finally, a single layer or the two layer compartment forming members are surrounded and coated with an outer wall. A passageway is laser, leached, or mechanically drilled through the wall to contact the drug layer. When the passageway is formed by a laser, the dosage form is optically-oriented automatically by the laser equipment for forming the passageway on the preselected surface for forming the passageway.

In another manufacture, dosage form 10 is manufactured by the wet granulation technique. In the wet granulation technique, for example, the drug and the ingredients comprising the drug-forming core or the drug-forming layers are blended using a solvent, such as ethyl alcohol-water 98:2 v:v (volume:volume) as the granulation fluid. Other granulating fluid, such as denatured alcohol 100%, can be used for the purpose. The ingredients forming the drug core or layers are individually passed through a 20 mesh screen and then thoroughly blended in a mixer. Next, other ingredients comprising the core or layers are dissolved in a portion of the granulation fluid, such as the cosolvent described above. Then, the latter prepared we blend is slowly added to the drug blend with continual mixing in the blender. The granulating fluid is added until a wet blend is produced, which wet mass then is forced through a 20 mesh screen onto oven trays. The blend is dried for 18 to 24 hours at 30° C. to 50° C.. The dry granules are sized then with a 20 mesh screen. Next, a lubricant is passed through screen, such as an 80-mesh screen, and added to the dry screen granule blend. The granulation is placed in a blender and blended for 1 to 15 minutes. A push layer is made by the same wet granulation techniques. The compositions are pressed into their individual layers in a HATA® layer press.

Another manufacturing process that can be used for providing the compartment-forming composition core or layers comprise blending the powdered ingredients for each core or layers independently in a fluid bed granulator. After the powdered are dry blended in the granulator, a granulating fluid for example, poly(vinyl)pyrrolidone) in water, or in denatured alcohol, or in 9:5 ethyl alcohol/water, or blends of ethanol and water is spray on the powders. Optionally, the ingredients can be dissolved or suspended in the granulating fluid. The coated powders are the dried in a granulator. This process granulates all the ingredients present therein while adding the granulation fluid. After the granules are dried, a lubricant such as stearic acid or magnesium stearate is added to the granulator. The granules for each separate core or layers are pressed then in the manner described below.

Dosage form 10 of the invention can be manufactured by mixing a drug with composition-forming ingredients and pressing the composition into a layer possessing dimensions that correspond to the internal dimensions of the compartment of the dosage form. In another manufacture the drug and other drug composition-forming ingredients and solvent are mixed into a solid, or a semisolid, by conventional methods such as ballmilling, shaking, calendaring, tumbling, stirring or rollmilling, and then pressed into a preselected layer-forming shape. Next, a layer of a composition comprising an osmopolymer and an optional osmagent are placed in contact with the drug layer. The layering of the first layer comprising the drug and the second layer comprising the osmopolymer and optional osmagent composition can be accomplished by using a conventional layer-press technique. The well can be applied by molding, brushing, spraying or dipping the pressed bilayer's shapes with wall-forming materials. Another and preferred technique that can be used for applying the wall is the air-suspension coating procedure. This procedure consists in suspending and tumbling the two contacting layers in current of air until the wall-forming composition surrounds the layers. The air suspension procedure is described in U.S. Pat. No. 2,799,241; *J Amer Pharm Assoc*, Vol 48 pp 451–454 (1979); and, ibid, Vol 49 pp 82–84 (1960). Other standard manufacturing procedures are described in *Modern Plastics Encyclopedia*, Vol 46 pp 62–70 (1969); and in *Pharmaceutical Science*, by Remington, 14th Ed, pp 1626–1678 (1970), Mack Publishing Co., Easton, Pa.

Exemplary solvents suitable for manufacturing the wall, a single layer and a bilayer core include inert inorganic and organic solvents final laminated wall. The solvents broadly include members selected for the group consisting of aqueous solvents, alcohols, ketones, esters, ethers, aliphatic hydrocarbons, halogenated solvents, cyclaliphatics, aromatics, hetercyclic solvents and mixtures thereof. Typical solvents include acetone, diacetone, alcohol, methanol, ethanol, ispropyl alcohol, butyl alcohol, methyl acetate ethyl acetate, isopropyl acetate, n-butyl acetate, methyl isobutyl ketone, methyl propyl ketone, n-hexane, n-heptane ethylene glycol monoethyl ether, ethylene glycol monoethyl acetate, methylene dichloride, ethylene dichloride, propylene dichloride, carbon tetrachloride, chloroform, nitroethane, nitropropane, tetrachlorethane, ethyl ether, isopropyl ether, cyclohexane, cyclooctane, benzene, toluene, naptha, tetrahydrofuran, diglyme, aqueous and nonaqueous mixture thereof, such as acetone and water, acetone and methanol, acetone and ethyl alcohol, methylene dichloride and methanol, and ethylene dichloride and methanol.

DETAILED DISCLOSURE OF EXAMPLES OF THE INVENTION

The following examples are merely illustrative of the present invention and they should not be considered as limiting the scope of the invention in any way as these examples and other equivalents thereof will become apparent to those versed in the art in the light of the present disclosure, the drawings and accompanying claims.

EXAMPLE 1

A dosage form for delivering the antiepileptic drug phenytoin is made as follows: first an antiepileptic drug layer is prepared by blending phenytoin, polyoxyethylene stearate, sodium carboxymethylcellulose, sorbitol and polyvinylpyrrolidone are blended into a homogenous mass. Then, anhydrous, denatured ethyl alcohol is added to the freshly prepared mass, with blending to produce a wet mass. Next, the ethyl alcohol is evaporated to yield a dry composition, and followed by the addition of magnesium stearate and the ingredients blended again to yield an antiepileptic drug composition.

Next, a displacement layer is prepared by blending into a homogenous blend sodium carboxymethylcellulose possessing a higher molecular than the sodium carboxymethylcellulose in the drug composition, sodium chloride, hydroxypropylmethylcellulose, ferric oxide and hydroxypropylcellulose are blended to yield an osmotic displacement composition. Then, water is added to the composition to produce a fluid bed granulate, followed by evaporating the water and then milling the dry blend accompanied by the addition of magnesium stearate.

The antiepileptic drug composition is next pressed in layered arrangement against the osmotic displacement layer, to provide a compressed bilayer core. The core next is coated with a subcoat comprising hydroxypropylcellulose, hydroxypropylmethlcellulose and water to coat the bilayer core. The water is removed by evaporation to provide the subcoated bilayer core. Then, a semipermeable wall is coated around the subcoated bilary core. The semipermeable wall is coated from a wall-forming composition comprising cellulose acetate, polyethylene glycol, polyvinylpyrrolidone and cosolvent acetone and methanol to apply the semipermeable well. The cosolvent is removed by evaporation and an orifice is drilled through the wall and the subcoat to connect the antiepileptic layer with the exterior of the dosage form.

EXAMPLE 2

The procedure of Example 1 is followed to provide a dosage form comprising the following: a drug layer comprising 50 wt % phenytoin, 28.5% wt % sodium carboxymethylcellulose comprising a 90,000 molecular weight, 9 wt % sorbitol, 3 wt % polyethylene glycol stearate, 9 wt % polyvinylpyrrolidone and 0.5 mg magnesium stearate; a displacement layer comprising 58.75 wt % sodium carboxymethycellulose comprising a 300,000 molecular weight, 30 wt % sodium chloride, 5 wt % hydroxypropylmethylcellulose comprising a 9,200 molecular weight, 5 wt % hydroxypropylcellulose comprising a 12,300 molecular weight, 1 wt % ferric oxide and 0.25 wt % magnesium stearate. The drug-osmotic bilayer core comprises a subcoat of 70 wt % hydroxypropylcellulose comprising a 38,000 molecular weight and 30 wt % hydroxypropylemthylcellulose comprising a 11,2000 molecular weight; and comprises a semipermeable wall comprising 80 wt % cellulose acetate comprising an acetyl content, and 20 wt % polyethylene glycol comprising a 3350 molecular weight. The dosage form comprised a 0.76 mm exit port.

EXAMPLES 3 and 4

Figure 6A:
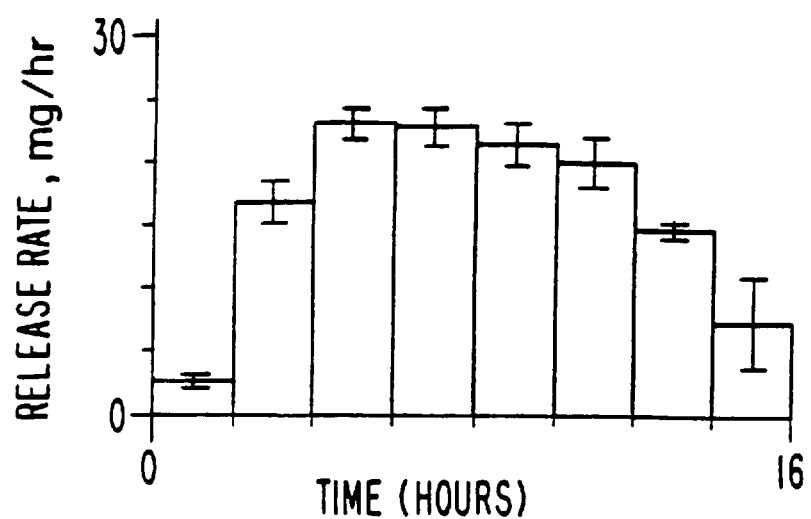
FIGS. 6A and 6B depicts the antiepileptic drug release rate for two dosage forms over two different times.
Figure 6B:
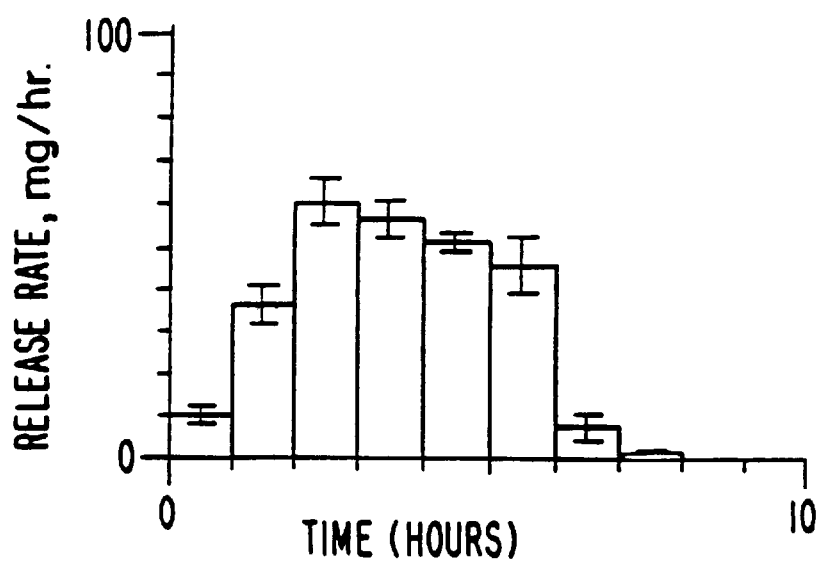

Two dosage forms are prepared according to the invention, wherein both dosage forms comprise 276 mg of phenytoin. One dosage form is manufactured with a slow rate of release that release 90% of the phenytoin in 14.7 hours at a release rate of 21mg/h as seen in drawing FIG. 6A; and a fast release dosage form that release 90% of the phenytoin in 5.7 hours at a release rate of 50 mg/h, as seen in drawing FIG. 6B. The slow release dosage form of drawing FIG. 6A comprised a semipermeable wall 0.101 mm thick and the fast release dosage form of drawing FIG. 6B comprised a semipermeable wall 0.025 mm thick. Each of the dosage forms are identical, except for the thickness of the semipermeable wall.

EXAMPLE 5

Figure 7:
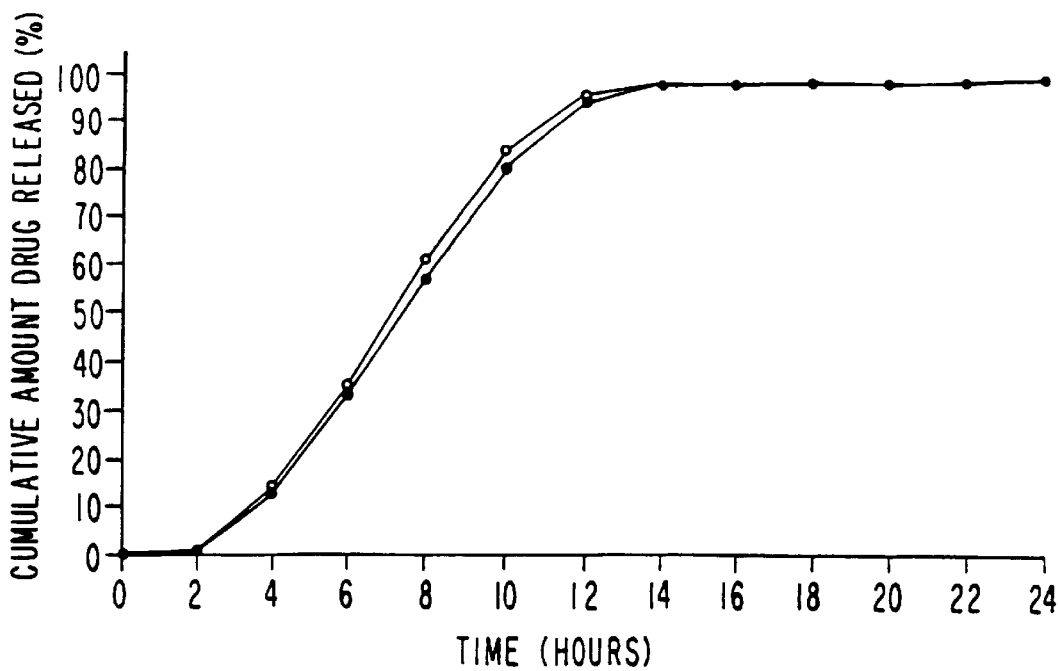
FIG. 7 depicts the release pattern for the dosage form in an acid and alkaline environment.

The dosage forms of the invention provides protection against an acid environment and against the alkaline environment of the gastrointesinal tract. The protection provided substantially lessens or substantially reduces the conversion of a drug from one therapeutically form to another therapeutically inactive form. The dosage form substantially eliminates a change of a drug from an active to an inactive form. In drawing FIG. 7, the protection for phenytoin against the effects of artificial gastric fluid is seen in the curved line with black circles and the protection against the effects of artificial intestinal fluid is seen in the curved line with clear circles.

EXAMPLE 6

Figure 8:
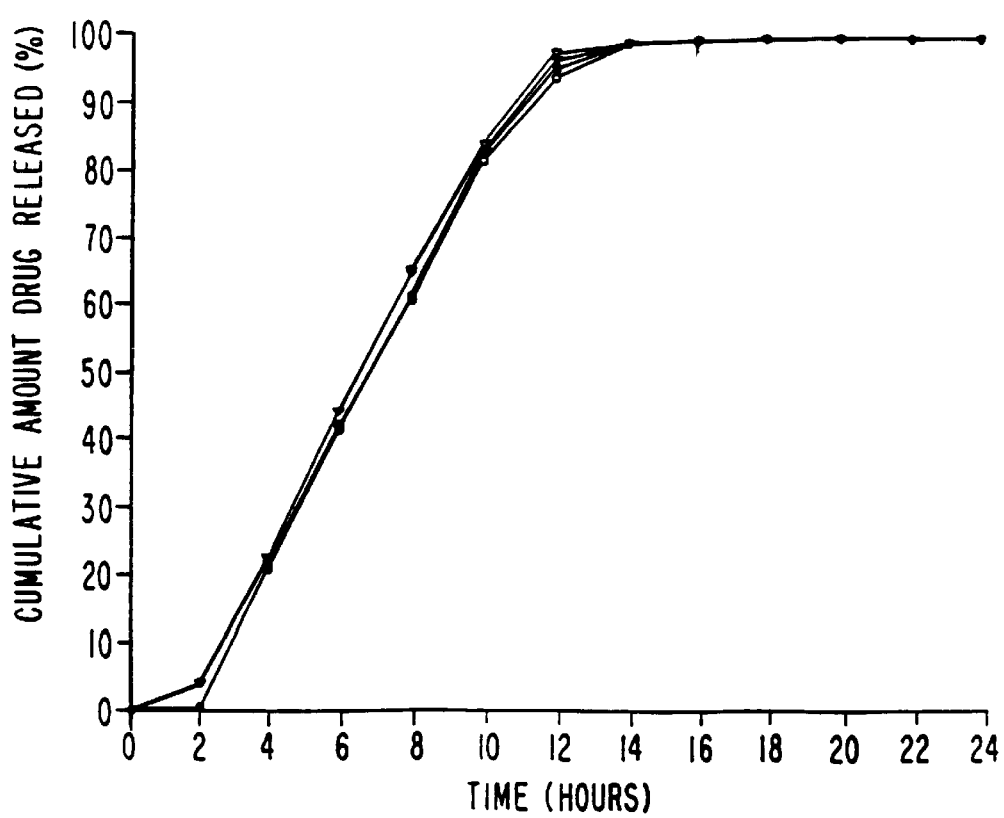
FIG. 8 depicts a drug release curve illustrating for this invention the delivery rate is independent of the size of the passageway.

The procedures of the above examples are followed in this example to provide four dosage forms for dispensing an antiepileptic drug, wherein the dosage forms are identical except for the size and the number of the exit passageways. The dosage forms are made comprising one passageway of 1.016 mm diameter, a dosage form with on 0.559 mm passageway, a dosage form comprising two 0.055 mm in diameter passageways, and a dosage form comprising three 0.559 mm passageways. The accompanying drawing FIG. 8 shows the cumulative amount of drug released form the dosage form for the different sized passageways and for the different number of passageways is independent of the environment of and free of the influence of fluid in the environment that contacts a passageway during operation of a dosage form. The dosage form of the invention prevents, for example, an alkali salt, such as a sodium salt of phenytoin, from a premature release from the dosage form coupled with the conversion of an alkali salt to a practically insoluble form in the gastrointestinal pH range of 1 to 8.

EXAMPLE 7

The procedure of the above examples are followed in this example to provide dosage forms of different geometries and to provide dosage forms having a high cumulative amount of drug release from the dosage form. The dosage forms provided are as follows: a dosage form comprising an oval shape with a surface area of 4.2 cm, a wall thickness of 0.14 mm and a T90 release rate of 13.2 hours; a dosage form comprising a solid vertical shape, a surface area of 4.1 cm, a wall thickness of 0.14 mm and a T90 release rate of 11.8 hours; and a dosage form comprising a round shape, a surface area of 4.0 cm, a wall thickness of 0.14 mm and a T90 release rate of 14 hours. The amount of drug, residual drug, remaining int he dosage form at the termination of the delivery period is for a dosage form comprising an oval shape 1.54%; for a dosage form comprising a round shape 0.85%; and for a dosage form comprising a vertical shape possessing a lengthwise axis larger than its cross-section, cross-sectional or perpendicular thereto is 0.12%. The results demonstrate a dosage form provided by the invention delivers substantially of its drug over time.

EXAMPLES 8 and 9

Figure 9:
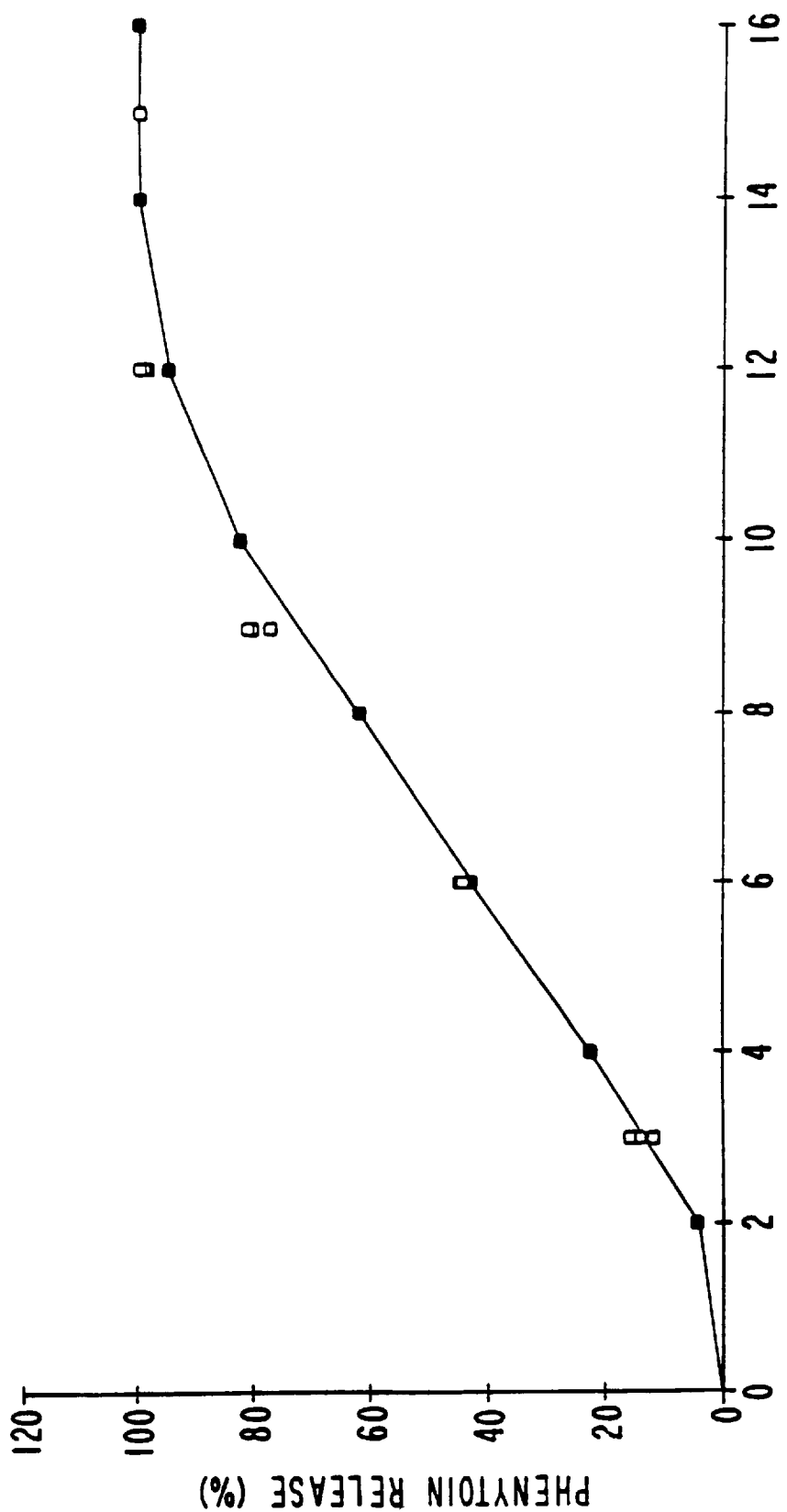
FIG. 9 illustrates the dosage form has substantially identical release patterns in vivo and vitro; and Drawing

Drawing FIG. 8, demonstrates the in vivo and in vitro drug release rate from a dosage from comprising the same structure and the same drug dose are substantially identical over a prolonged time. In the drawing figure, the clear squares depict the in vivo release rate determined by measuring the dose of phenytoin released at various time intervals from a dosage from as it moves through the gastrointestinal tract of a laboratory animal. The black squares indicate the dose of phenytoin released at a corresponding time interval measured in a distilled water bath. Drawing FIG. 9 demonstrates the invention comprising means for maintaining the integrity of the wall of the dosage form and correspondingly substantially lessening and/or preventing wall cracking during operation of the dosage form as the dosage form osmotically and hydrodynamically pumps a drug in a water bath. In drawing FIG. 10, the black squares indicate a dosage form made with a single wall without a subcoat, which wall appeared to crack at one hour that resulted in the loss of osmotic and hydrodynamic pressure in the dosage form. The white squares depict the release rate for a dosage form wherein the wall is supported by a subcoat that enables the semipermeable wall to keep its integrity and maintain an osmotic and hydrodynamic pressure in the dosage form during the life of the dosage form which results in substantially all the drug delivered from the dosage form.

EXAMPLE 10

A dosage form is prepared as follows: first 250 mg of carbamazepine, a white practically insoluble in water antiepileptic drug, is passed through a 40 mesh screen, and then rescreened with sodium carboxymethylcellulose, polyvinylpyrrolidone, and sorbitol. The ingredients are blended on a blender for 15 minutes then transferred to a granulation bowl. With constant stirring, ethanol is added to the continuous blend with blending continued until a homogenous blend is produced in the granulator. Then, the blend is passed through a 20 mesh screen. The screened granules are spread over a tray and placed in an oven to a moisture content of 2%. Then, the dried granulation is passed through a 20 mesh screen and transferred to a blender. Next, magnesium stearate is passed through a 60 mesh screen, added to the blender and mixed for two minutes.

Next, hydroxypropylcellulose is added to distilled water and blended for two hours. Then, sodium chloride is screened through a 20 mesh screen and blended with sodium carboxymethylcellulose possessing a higher molecular weight, hydroxypropylmethlcellulose and ferric oxide, and all the ingredients blended for 5 minutes. The blend is screened and transferred to a granulation bowl and pre-screened magnesium stearate is added to the mixing bowl, followed by mixing for seven to eight minutes.

Then, 550 mg of the carbamazepine composition and 220 mg of the displacement push composition are transferred into a vertical die possessing a lengthwise axis longer than the cross-section axis and the layers pressed under one ton of pressure for each layer, to yield a solid capsule-shaped two layer core.

Next, hydroxypropylcellulose and hydroxypropylmethyl-cellulose are blended to provide a 70/30 ratio, respectively. Then, in a mixing vessel, distilled water is added to give a 6% solid content, with constant stirring to give a smooth homogenous solution, which is an suspension homogenous solution, which is air suspension coated around the core to yield the subcoated core. Then, cellulose acetate, polyvinyl-pyrrolidone and polyethylene glycol are mixed with acetone and methanol in a ratio or 80/20 (wt/wt) to achieve a solid content of 5% and the subcoated core is overcoated in an air suspension machine with a semipermeable wall. then the dosage forms are dried to substantially free the dosage form of solvents. Next, a 30 ml (0.76 mm) exit port is drilled through the semipermeable wall and the subcoat to connect the carbamazepine drug layer with the exterior of the dosage form.

EXAMPLE 11

The procedure of Example 10 is followed to provide a dosage form as follows: and antiepileptic drug layer composition comprising 250 mg of ethotoin, 157 mg of sodium carboxymethlcellose of 80,000 molecular weight, 50 mg of polyvinylpyrrolidone, 50 mg of sorbitol, 17 mg of polyoxyethylene stearate, and 3 mg of magnesium stearate; a displacement layer composition comprising 130 mg of sodium carboxymethylcellulose of 300,000 molecular weight, 67 mg of sodium chloride, 11 mg of hydroxypropylmethlcellulose of 11,200 molecular weight, 11 mg of hydroxypropylcellulose of 28,000 molecular weight, 2 mg of ferric oxide and 0.6 mg of magnesium stearate. The dosage form comprises a subcoat of 21 mg hydroxypropylcellulose and 9 mg hydroxypropylmethylcellulose; and a semipermeable wall comprising 58.8 mg of cellulose acetate and 14.7 mg of polyethylene glycol. The dosage forms provided by this example comprises additional a semipermeable wall of 44 mg of cellulose acetate and 11 mg of polyethylene glycol. The dosage form comprising the higher amount of cellulose acetate is a slow release dosage form and the dosage form comprising the lesser amount of cellulose acetate is a fast release dosage form.

EXAMPLE 12

The procedures of the above examples are followed to provide a dosage form comprising an antiepileptic drug selected from the group consisting of mephenytoin, phenobarbital, primidone, ethosuximide, methosuximide, phensuximide, trimethadione, clonazepam, clorazepate, clobazam, felbamate, vigabatin, gabapentin and tioridone.

EXAMPLE 13

A dosage form is provided by following the above examples to provide a dosage form comprising a drug layer comprising 45 wt % phenytoin, 46.5 wt % polyethylene glycol of 300,000 molecular weight, 3 wt % of polyvinylpyrrolidone of 30,000 molecular weight, 0.50 wt % calcium stearate, and 5 wt % of polyethylene glycol monolaurate; an osmotic layer comprising 58.75 wt % of a polyethylene oxide having 7,500,000 molecular weight, 30 wt % of sodium chloride, 5 wt % of hydroxy-propylmethylcellulose possessing a 9,200 molecular weight, 1 wt % of ferric oxide, 0.25 wt % of calcium stearate and 5 wt % of hydroxypropylcellulose possessing a 30,000 molecular weight, an internal coat that enrobes the drug and osmotic layers, which enrobing coat comprises 95% wt % hydroxyethylcellulose a nonionic water soluble polymer and 5 wt % of polyethylene glycol; and an outer semipermeable wall comprising 85 wt % cellulose acetate having 39.8% acetyl content, and 15 wt % polyethlene glycol. The dosage form had a mean release rate of 23,745 mg/hr, one 1 mm passageway, and a T90 pf 12.9 hours. The semipermeable wall of this dosage form is 0.15 mm thick.

EXAMPLE 14

The procedure of Example 13 is followed in this example, with all procedures as set forth previously except that in this example the dosage form comprises a semi-permeable wall 0.025 mm thick, a T90 of 6 hours, and a man release rate of 46.19 mg/hour.

EXAMPLE 15

An exterior, quick release coat comprising the antiepileptic drug carbamazepine as adjunct therapy to slow release phenytoin from the interior of the dosage form comprises blending carbamazepine with a member selected from the group consisting of a water-binder, water-soluble film-former polymer selected from the group consisting of hydroxyethylcellulose, hydroxypropylcellulose and hydroxymethycellulose are added to a fluid bed granulator and the materials blended in a moving current air. Then, a granulating fluid is sprayed onto the fluidizing powders until the powders are agglomerated. Then, the fluidizing process is continued until the granulation is dry. The prompt release coat is compressed or air sprayed around the external surface of the semipermeable wall to yield a prompt release coat of antiepileptic drug and a slow release antiepileptic drug from a single dosage form.

EXAMPLE 16

The procedure of Example 15 is followed to yield a single dosage form comprising an antiepileptic drug combination with one antiepileptic drug in releasable contact with the exterior surface of the dosage form and a different antiepileptic drug in extended releases in the interior of the dosage form. Examples of antiepileptic combinations comprises phenytoin and phenobarbitone; phenytoin and carbamazepine, phenobarbitone and carbamazepine, felbamate and carbamazepine, phenobarbitone and primidone, carbamazepine and primidone, carbamazepine and clonazepam, carbamazepine and clorazepate, phenytoin and clonazepam, phenytoin and clorazepate, phenytoin and felbamate, phenytoin and vigabatron, and phenytoin and gabapentin.

Method of Using the Invention for Antiepileptic Therapy

An embodiment of the invention pertains to a method for delivering an antiepileptic drug orally to a patient in need of antiepileptic therapy, which method comprises the steps (A) an admitting into the patient a dosage form comprising (1) an antiepileptic drug layer comprising a dosage amount of an antiepileptic therapeutic program; (2) a push layer comprising means for imbibing fluid for expanding for pushing the antiepileptic layer from the dosage form; (3) an internal coat for maintaining the structural integrity of the dosage form and for maintaining an osmotic and hydrodynamic pressure surrounding the antiepileptic drug layer and the push layer; (4) a semipermeable wall surrounding the internal coat with semipermeable wall is permeable to fluid flux and impervious to the flux of an antiepileptic drug; (5) a passageway in the dosage form for releasing the antiepileptic drug from the dosage form; (B) imbibing fluid through the semipermeable wall at a rate determined by the permeability of the semipermeable wall and the osmotic pressure gradient across the semipermeable wall causing the push layer to expand; and (C) deliver the antiepileptic drug from the dosage form through the passageway to the patient over a prolonged period of time. The method comprises further positioning the dosage form buccally of sublingually for buccal antiepileptic therapy or sublingual antiepileptic therapy.

In summary, it will be appreciated the present invention contributes to the antiepileptic art an unobvious dosage form that possess a practical utility. can administer an antiepileptic drug in a prompt dose and in a known dose release per unit time over time. While the invention has been described and pointed out in detail with reference to operative embodiments thereof, it will be understood to those skilled in the antiepileptic art that various changes, modifications, substitutions and omissions can be made without departing from the spirit of the invention. It is intended, therefore, that the invention embrace those equivalents within the scope of the claim which follow.

We claim:

1. A dosage form for orally administering phenytoin to a patient in need of an antiepileptic drug, wherein the dosage form comprises;

(a) a dosage amount of phenytoin in the dosage form;

(b) a composition comprising a member selected from the group consisting of a polyalkylene and a carboxyalkylcellulose in the dosage form;

(c) an internal coat that surrounds at least the dosage amount of phenytoin for aiding in maintaining the integrity of the dosage form and for protecting the phenytoin in the dosage form;

(d) an external coat that contacts the internal coat and surrounds and defines the dosage form for use in antiepileptic therapy; and, (e) an exit in the dosage form for releasing the phenytoin from the dosage form to the patient in need of antiepileptic therapy.

2. The dosage form for administering the antiepileptic drug according to claim 1, wherein the phenytoin is replaced by an antiepileptic drug selected from the group consisting of sodium phenytoin, potassium, phenytoin, mephenytoin, phenobarbital, primidone, carbamazepine, ethosuximide, methsuximide, phensuximide, trimethadione, clonazepam, clorazepate, phenacemide, paramethadione, primaclone, clobazam, felbamate, flunarizine, lamotrigine, progabide, virgabatim, eterobarb, gabapentin, oxcarbazepine, ralitoline, tiagobine, sulthiame and tioridone.

* * * * *